(12) United States Patent
Cunningham et al.

(10) Patent No.: US 10,487,537 B2
(45) Date of Patent: Nov. 26, 2019

(54) CLEANING DEVICE FOR DOOR HANDLES AND PUSH PLATES

(71) Applicants: Brian Cunningham, Dublin (IE); Maurice McDonagh, Dublin (IE)

(72) Inventors: Brian Cunningham, Dublin (IE); Maurice McDonagh, Dublin (IE)

( * ) Notice: Subject to any disclaimer, the term of this patent is extended or adjusted under 35 U.S.C. 154(b) by 95 days.

(21) Appl. No.: 15/670,383

(22) Filed: Aug. 7, 2017

(65) Prior Publication Data

US 2018/0023317 A1    Jan. 25, 2018

Related U.S. Application Data

(63) Continuation of application No. 14/434,908, filed as application No. PCT/EP2013/071330 on Oct. 11, 2013, now abandoned.

(30) Foreign Application Priority Data

Oct. 20, 2012    (IE) .................................. S2012/0458

(51) Int. Cl.
*A61L 2/22*        (2006.01)
*E05B 1/00*        (2006.01)
*B08B 3/02*        (2006.01)

(52) U.S. Cl.
CPC .............. *E05B 1/0069* (2013.01); *A61L 2/22* (2013.01); *B08B 3/02* (2013.01)

(58) Field of Classification Search
CPC .......... E05B 1/003; E05B 1/0069; A61L 2/22; A61L 9/14; B08B 3/02; B65D 83/267; B65D 83/386
See application file for complete search history.

(56) References Cited

U.S. PATENT DOCUMENTS

| 2,602,700 | A | 7/1952 | Ryan |
| 3,173,579 | A | 3/1965 | Curie et al. |
| 3,994,440 | A | 11/1976 | Mancini |
| 4,046,508 | A | 9/1977 | McDonald |
| 5,016,781 | A | 5/1991 | Ten Wolde |
| 5,598,954 | A | 2/1997 | Salzano |

(Continued)

FOREIGN PATENT DOCUMENTS

| DE | 2846203 | 4/1980 |
| GB | 2402622 | 12/2004 |

(Continued)

OTHER PUBLICATIONS

International Search Report and Written Opinion for PCT/EP2013/071330, the international counterpart to U.S. Appl. No. 14/434,908.

*Primary Examiner* — David G Cormier
(74) *Attorney, Agent, or Firm* — Warner Norcross + Judd LLP

(57) ABSTRACT

A cleaning device for door handles and door push plates comprising a housing (60) for mounting on a door, the housing having a reservoir (76) of disinfectant liquid and a spray head (71), an actuating arm (72) which projects outwardly from the housing and is in use operatively associated with a door frame in which the door is mounted, such that opening or closing of the door causes movement of the actuating arm (72) to operate the spray head and to spray a disinfectant liquid onto the door handle, door push plate or other door surface, wherein the actuating arm engages with the door frame to operate the spray head.

7 Claims, 13 Drawing Sheets

(56) References Cited

U.S. PATENT DOCUMENTS

| | | |
|---|---|---|
| 6,029,600 A | 2/2000 | Davis |
| RE38,023 E | 3/2003 | De Laforcade |
| 6,968,982 B1 | 11/2005 | Burns |
| 7,080,427 B1 | 7/2006 | Campopiano et al. |
| 7,320,418 B2 | 1/2008 | Sassoon |
| 7,360,674 B2 | 4/2008 | Sassoon |
| 2002/0134798 A1 | 9/2002 | Lamboux |
| 2004/0026530 A1 | 2/2004 | Callueng |
| 2006/0153733 A1 | 7/2006 | Sassoon |
| 2006/0243762 A1 | 11/2006 | Sassoon |
| 2008/0023497 A1 | 1/2008 | Sassoon |
| 2008/0305020 A1 | 12/2008 | Oshmyansky |
| 2012/0251387 A1 | 10/2012 | Samaras |

FOREIGN PATENT DOCUMENTS

| | | |
|---|---|---|
| WO | WO2008141759 A2 | 11/2008 |
| WO | 2012130577 A2 | 10/2012 |
| WO | 2014057110 A1 | 4/2014 |

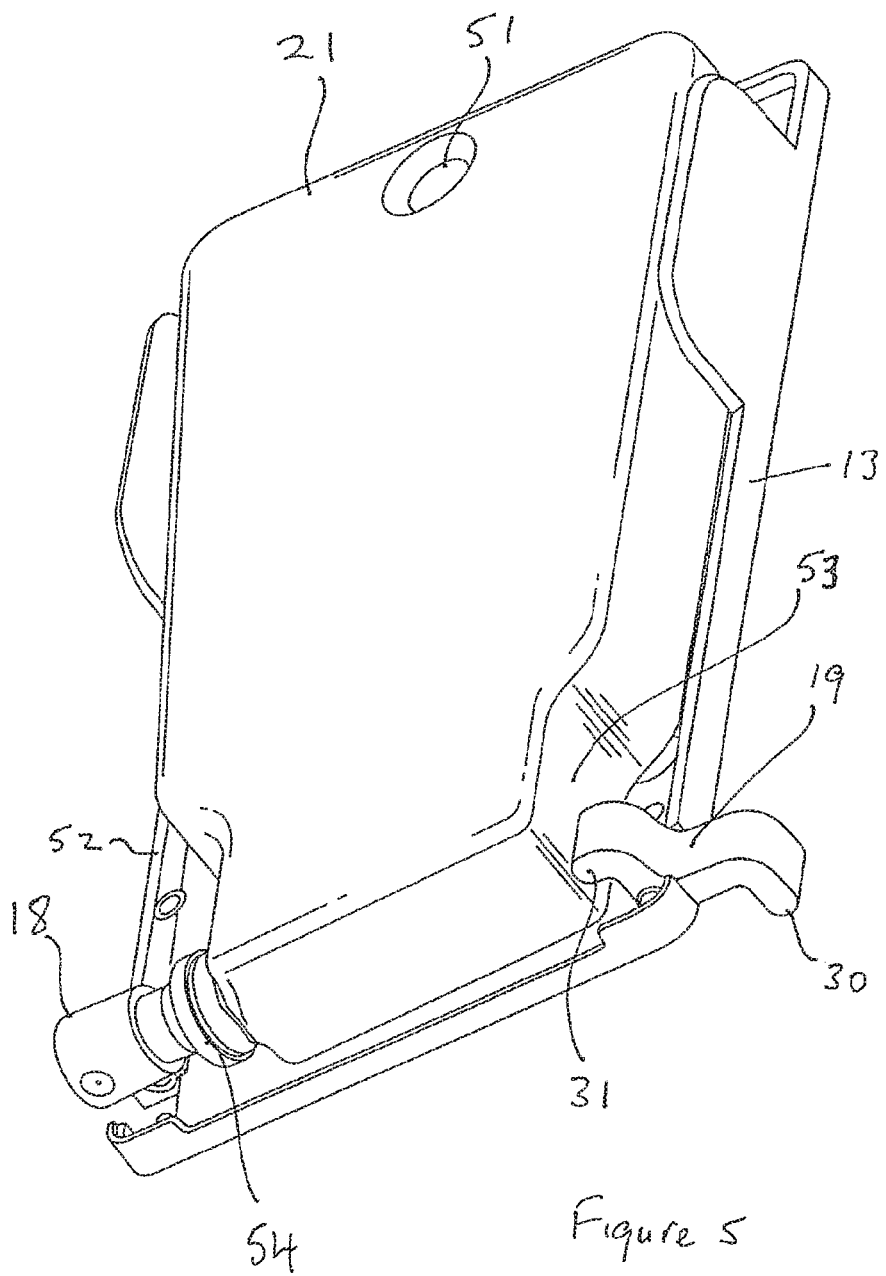

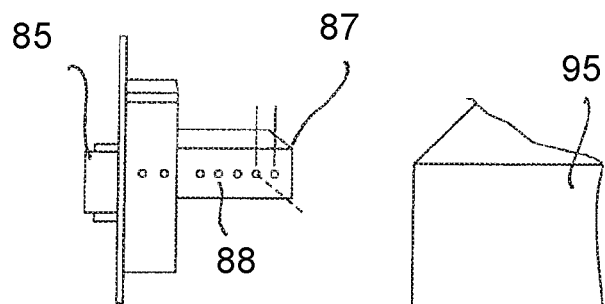
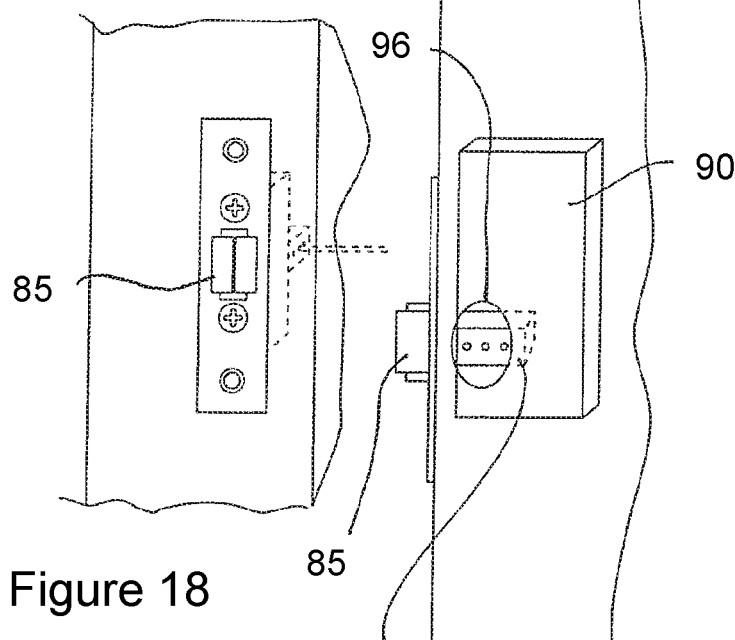
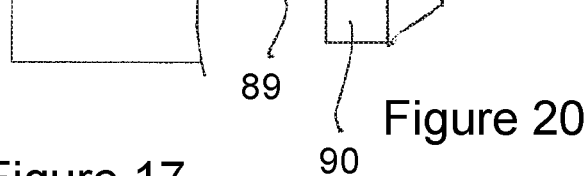

CLEANING DEVICE FOR DOOR HANDLES AND PUSH PLATES

CROSS-REFERENCE TO RELATED APPLICATIONS

This application is a continuation of, and claims priority to U.S. patent application Ser. No. 14/434,908 filed Apr. 10, 2015 by Brian Cunningham and Maurice McDonagh entitled CLEANING DEVICE FOR DOOR HANDLES AND PUSH PLATES. The Ser. No. 14/434,908 application is a 371 of international application No. PCT/EP2013/071330 filed Oct. 11, 2013 entitled CLEANING DEVICE FOR DOOR HANDLES AND PUSH PLATES, which claims benefit of Irish Application No. S2012/0458 filed Oct. 12, 2012.

BACKGROUND OF THE INVENTION

The present invention relates to a cleaning device for door handles and push plates. In particular the invention will have application in relation to cleaning toilet door handles.

Toilet door handles are often contaminated by many individuals who fail to wash their hands and these door handles become the source of general contamination in public areas. A particular problem arises in hospitals and other establishments where there is likely to be a considerable amount of bacteria or other germs. In view of this problem, many individuals often try to open toilet doors with the minimum amount of physical contact with the door.

According to the invention there is provided a cleaning device for door handles and door push plates comprising a housing for mounting on a door, the housing having a reservoir of disinfectant liquid and a spray head, an actuating arm which projects outwardly from the housing and is in use operatively associated with a door frame in which the door mounted, such that opening or closing of the door causes movement of the actuating arm to operate the spray head and to spray a disinfectant liquid onto the door handle, door push plate or other door surface, wherein the actuating arm engages with the door frame to operate the spray head.

Preferably the apparatus arranged such that closing of the door causes movement of the actuating arm to operate the spray head.

In another preferred embodiment, preferably opening of the door causes movement of the actuating arch to operate the spray head.

Further preferably the actuating arm engages directly with the door frame when the door is in a closed position.

Preferably the actuating arm is pivotably mounted in the housing.

In one embodiment of the invention preferably the actuating arm has a door engaging portion.

More preferably, the door engaging portion projects forwardly of the plane of the housing which abuts the door.

The actuating arm has an actuating portion preferably disposed within the housing, to move a slidable arm (slider).

Preferably the actuating portion comprises a cam portion and as door is closed the cam portion causes movement of a sliding arm to actuate the spray head.

Further preferably as the door is opened, the cam portion is released so that the spray head acts against the sliding arm to move the sliding arm and cam portion to its initial position.

The spray head is in liquid communication with a reservoir of disinfectant fluid contained within the housing.

The reservoir of liquid is preferably mounted above the spray head.

The spray head preferably has a boss and a spray nozzle.

The container is preferably connected to the spray head via a conduit. The conduit is preferably connected to a connector needle which is mounted in a boss.

In another embodiment of the invention, the housing has a container of disinfectant fluid, said container being movable within the housing.

The container is preferably pivotably mounted within the housing.

Preferably the movement of the actuating portion of the actuating arm as the door is closed causes movement of the container within the housing.

Further preferably the container is connected to a spray head so that movement of the container causes operation of the spray head to spray a charge of disinfectant liquid.

As the door is opened, preferably the actuating arm is released to release the cam portion so that the bias of the spray head returns the container and cam portion to the initial position.

The cam portion preferably acts directly on a side wall of the container.

The container and spray head may be one unit which is replaceable when the liquid in the container is depleted.

The housing preferably has a cover.

The spray head is preferably arranged to operate on closing of the door.

Preferably the door handle may be elongate and further preferably may be rotatable.

The reference to a door handle will also include a push plate mounted on a door surface or indeed a particular portion of a door surface. The invention therefore provides an apparatus for applying a disinfectant to a door surface each time a door is opened or closed. The door surface may include one or more push plates.

Embodiments of the invention will now be described by way of example with reference to the accompanying drawings in which:

FIG. 5 is a perspective view of another embodiment of a cleaning device according to the invention;

FIG. 17 is a schematic view of another embodiment of cleaning apparatus according to the invention mounted on a door;

FIG. 18 is a partial end view of the door or FIG. 17 with an operating arm mechanism mounted therein;

FIG. 19 is a schematic view of the operating arm mechanism of FIG. 18; and

FIG. 20 is a schematic view of the cleaning apparatus of FIG. 17 with a trigger pin.

Figure 1:
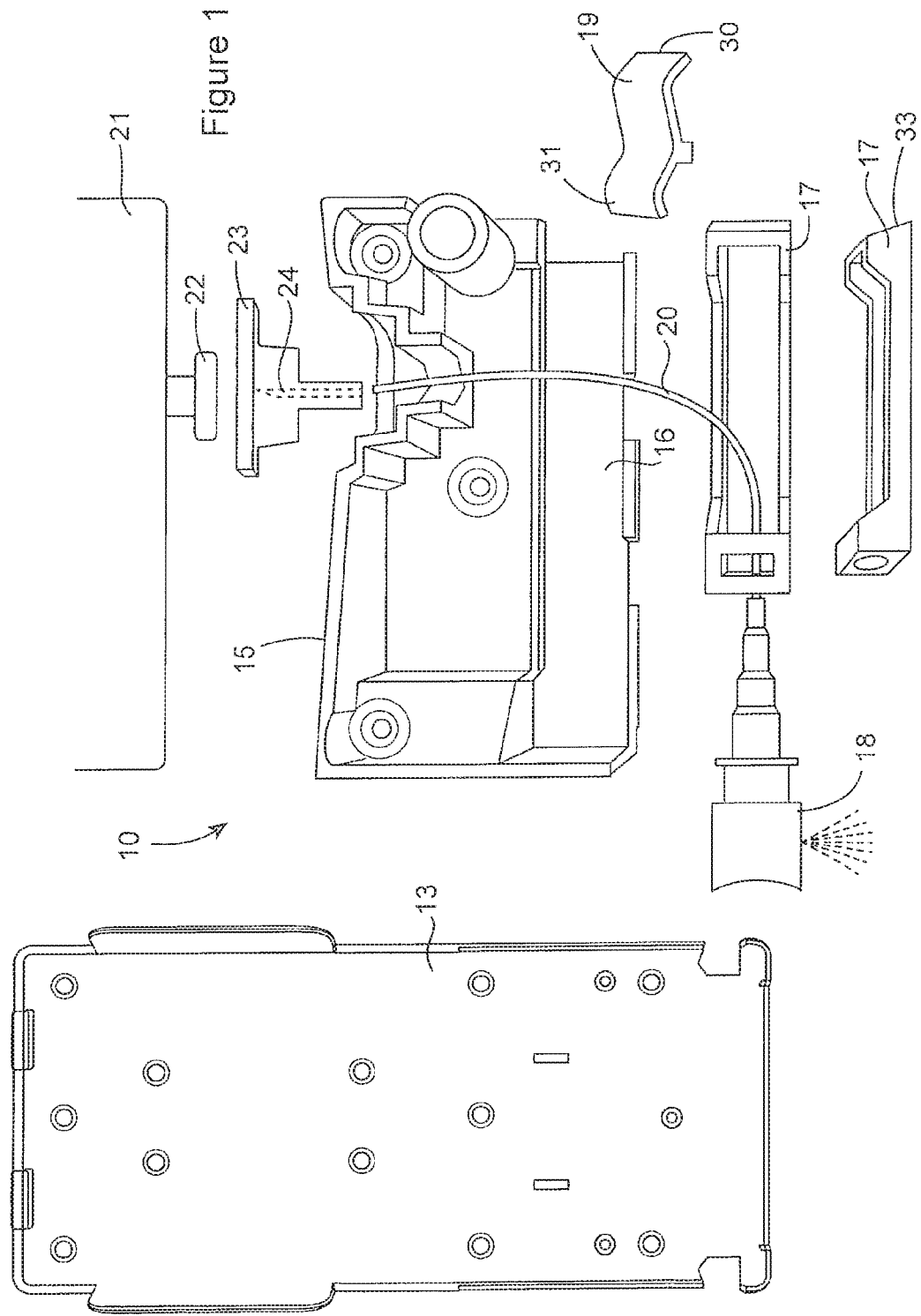
FIG. 1 is an exploded perspective view of an embodiment of a cleaning device according to the invention.

Referring now to the drawings wherein similar numerals will be used to indicate like parts, there is shown therein a cleaning device for door handles and push plates generally indicated at 10 according to the invention. At the outset, it is pointed out that the apparatus may be constructed to be fitted to a door which opens from the left hand side or the right hand side and the device will be constructed accordingly.

It will further be understood that the device may be used on the inside or outside of a door and may be used on a door which opens inwardly or outwardly.

Figure 4B:
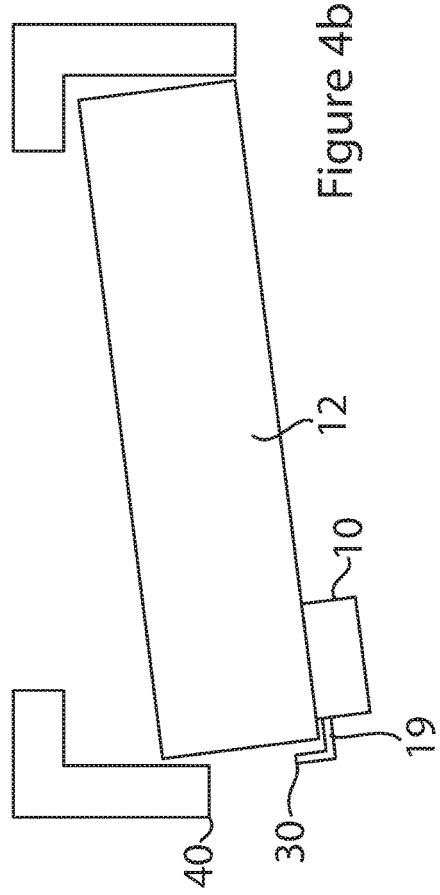
FIG. 4b is a schematic view of the cleaning device with the door in an open position.
Figure 4C:
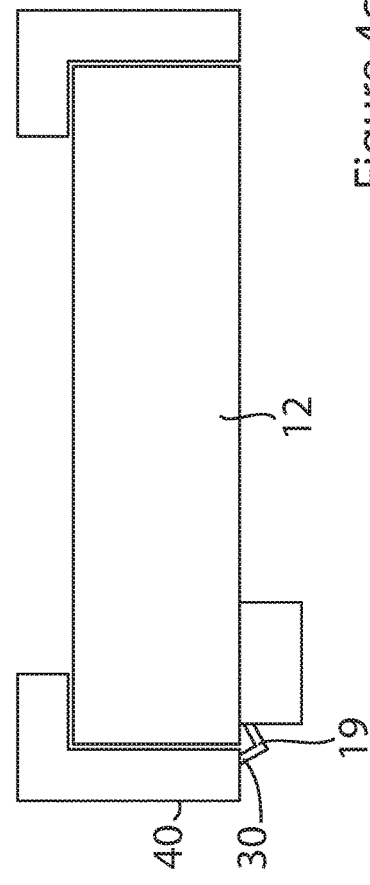
FIG. 4c is a schematic view of the cleaning device with the door in a closed position.
Figure 4A:
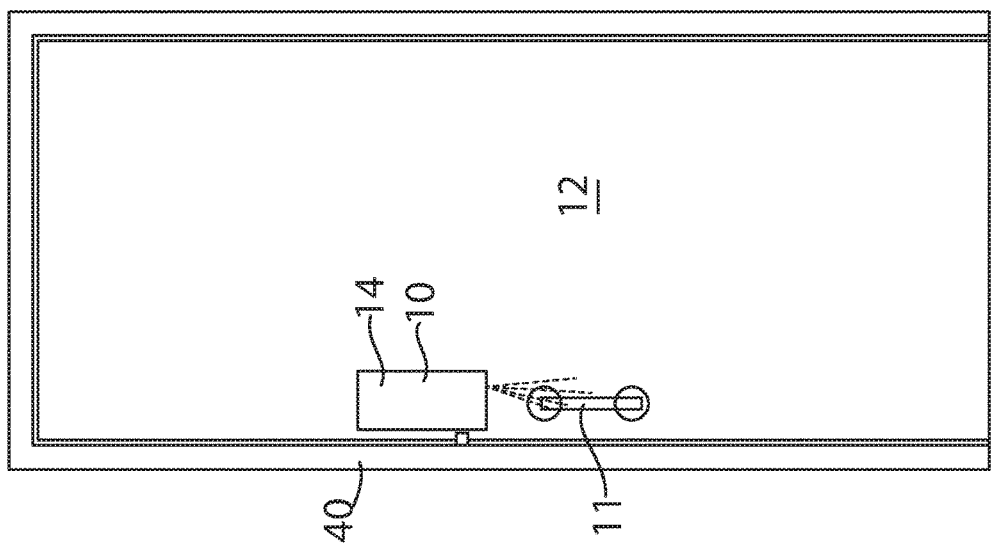
FIG. 4a is a schematic view of the apparatus of FIGS. 2 and 3 fixed on a door.
Figure 6:
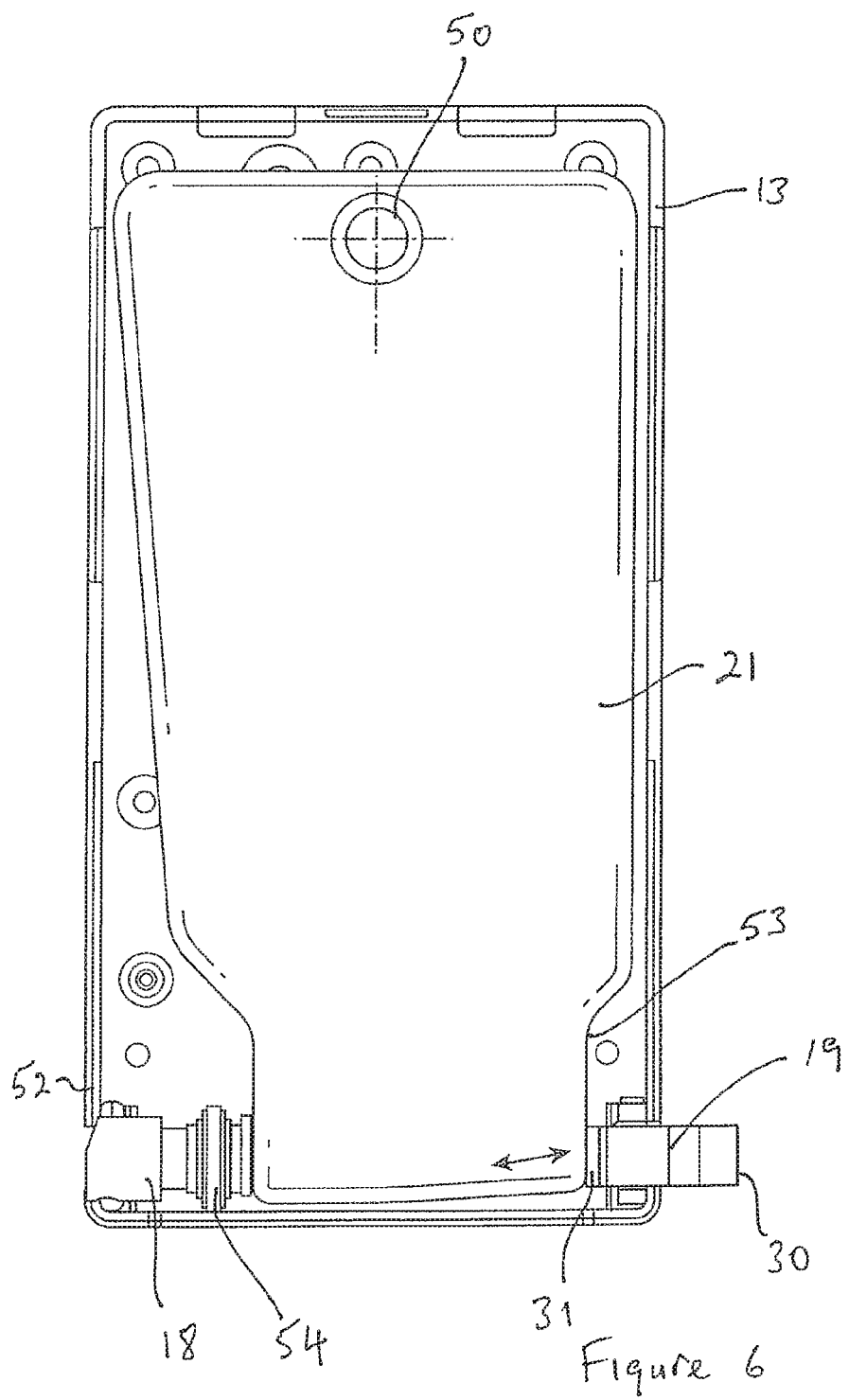
FIG. 6 is a front view of the apparatus of FIG. 5.

The apparatus or device 10 is for dispensing a spray of disinfectant liquid onto a handle 11 or a push plate (not shown) mounted on a door 12 (FIG. 4a).

Figure 2:
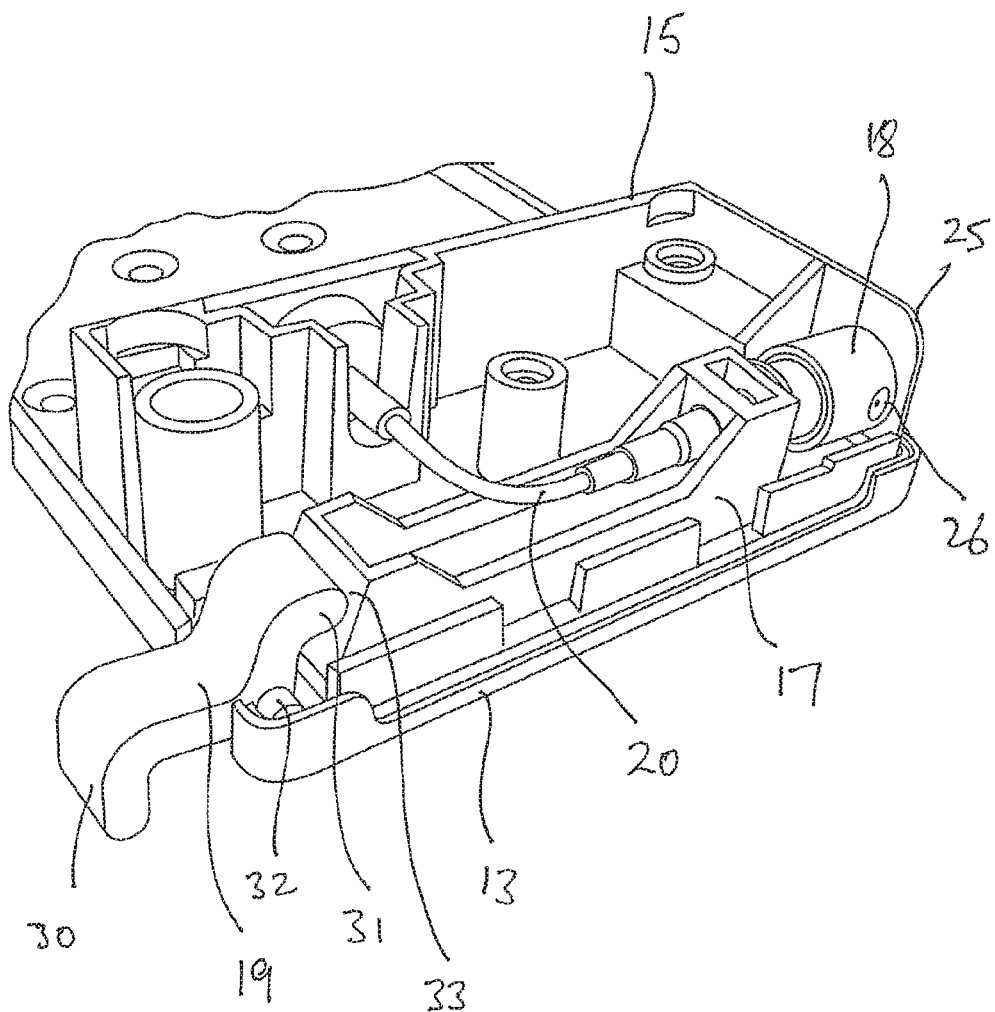
FIG. 2 is a perspective view of another embodiment of a cleaning device according to the invention.
Figure 3:
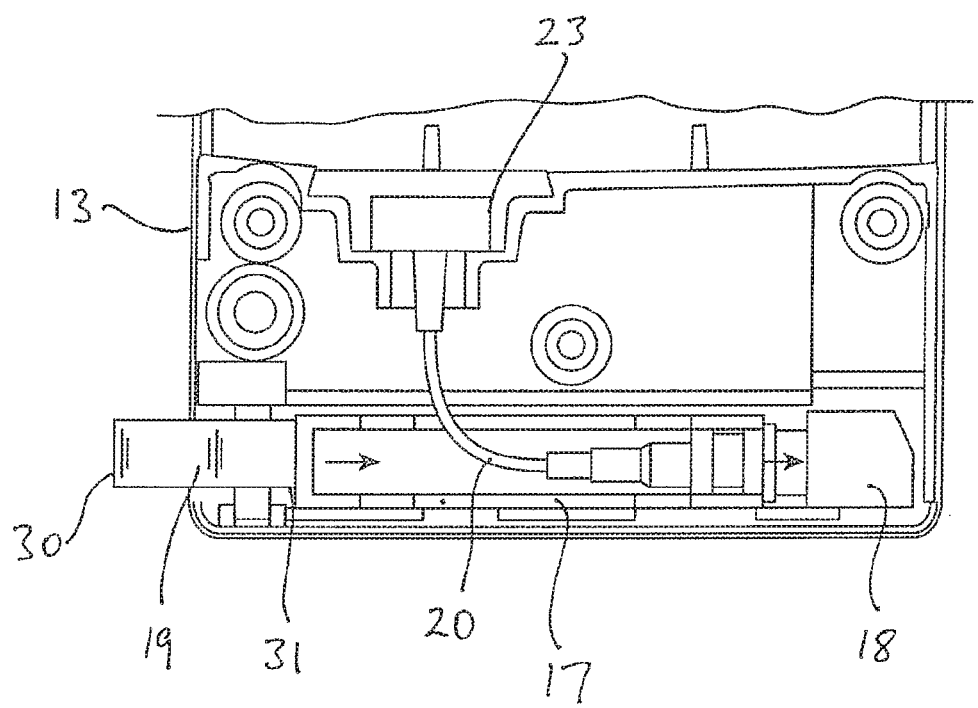
FIG. 3 is a front view of the apparatus of FIG. 2.

The apparatus 10 comprises a housing having a base plate 13 and a cover 14. In FIGS. 1-3, there is shown a frame 15 which is mounted to the base 13. The frame 15 has a slot 16 for accommodating a slideable arm (slider) 17 which can slide axially in the slot 16.

A spray head 18 is disposed at one end of the frame 15. An actuating arm 19 is mounted at the opposite end of the base 13 to the spray head 18 and projects laterally outwardly from the apparatus 10. The spray head is connected by a conduit 20 to a container of disinfectant liquid 21 which is also mounted on the base 13. The container 21 has a nipple 22 which is accommodated in a boss 23, the boss 23 having a needle 24 which is connected to the conduit 20 so that a replacement bottle can be readily engaged with the needle 24 when a new bottle is being put in place. It will be appreciated that the container 21 in this embodiment could be a flexible bag or pouch type of liquid container, or a solid walled container.

The base 13 and the cover portion 14 together provide an enclosed housing to secure the various components of the apparatus.

The construction shown in FIG. 1 is to be mounted on a door which opens from the right hand side whereas the construction shown in FIGS. 2 and 3 is to fitted to a door which opens on the left hand side.

As shown more clearly in FIGS. 2 and 3, the spray head 18 is disposed between an end wall 25 of the frame 15 and the slidable arm (slider) 17. The spray head has an aperture 26 for spraying a charge of liquid downwardly through an opening in the housing onto a door handle or push plate 11.

The actuating arm 19 has a door frame engaging portion 30 and a cam portion 31. The cam portion 31 is disposed within the housing and the door engaging portion projects forwardly of the plane of the base 13 which abuts the door surface to which it is fitted in use. The actuating arm 19 is pivotally mounted on the base 13 at 32.

The cam portion 31 engages a cam surface 33 on the slider 17 so that movement of the cam portion 31 against the slider 17, causes the slider to move against the spray head 18 and cause activation of the spray head to produce a spray of liquid.

As shown more clearly in FIGS. 3 and 4a-4C, in the open position of the door, the door frame engaging portion 30 of the actuating arm 19 projects slightly adjacent the edge of the door as shown clearly in FIG. 4b. As the door is closed (FIG. 4c) the door frame engaging portion 30 engages 20 with the door frame 40 causing the actuating arm 19 to pivot and causing the cam portion 31 to engage the cam surface 33 of the slider 17. The slider 17 therefore moves against the spray head to activate the spray head and produce a spray of liquid onto the handle 11. When the door is opened again, a spring bias in the spray head pushes against the slider 17 causing the actuating arm 19 to pivot and return to its initial position.

It will be appreciated that the handle 11 may be freely rotatable about its vertical axis. In another embodiment, the handle may be mounted horizontally or it may be a conventional handle.

In this embodiment, when it is desired to replace the container of disinfectant liquid 21, it is a simple matter to remove the cover 14 from the base of the unit and to replace the container 21.

Referring now to FIGS. 5-12 there is shown therein another embodiment of the invention. In this embodiment, the housing has a base 13 which holds a container of disinfectant fluid 21 and the container 21 is moveable within the housing. The container is pivotably mounted on the base 13 by a boss 50 on the base projecting through an aperture 51 in the container. The container 21 has mounted thereon a spray head 18 and the spray head 18 abuts a side wall 52 of the base 13. The actuating arm 19 is mounted on the base 13 so that the cam portion 31 engages a side wall 53 of the container 21. The spray head 18 may be attached to the container 21 via a boss 54 or indeed may be integral with the container 21.

In this embodiment the container 21 is of a solid wall construction being substantially rigid to enable it to be moved by the actuating arm 19. The container 21 and spray head 18 may be supplied as a refill unit, enabling easy replacement of the disinfectant when it needs to be replenished.

Figure 7:
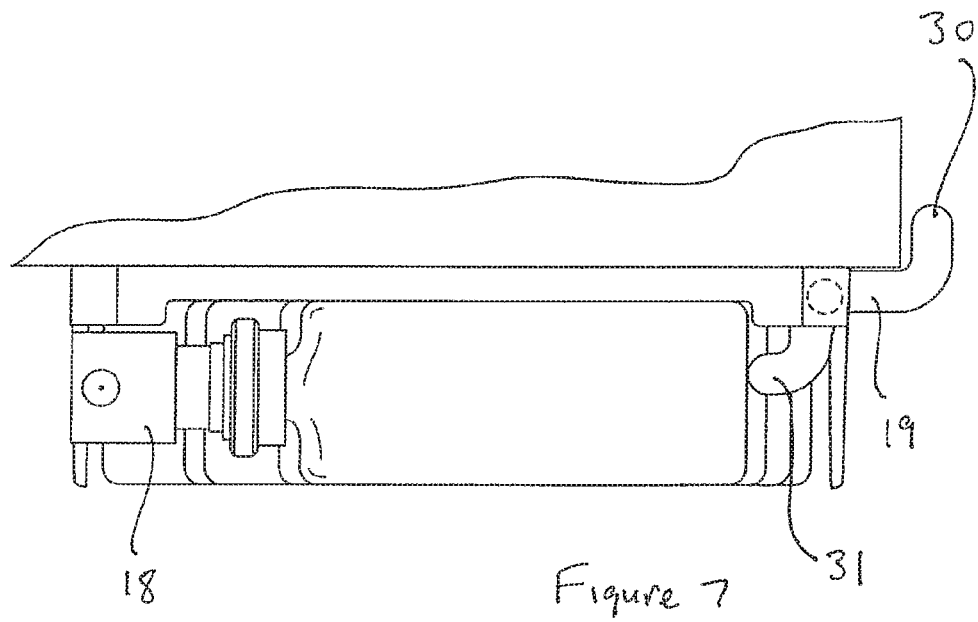
FIG. 7 is an underneath schematic view of the apparatus of FIG. 6 with the door in an open position.
Figure 8:
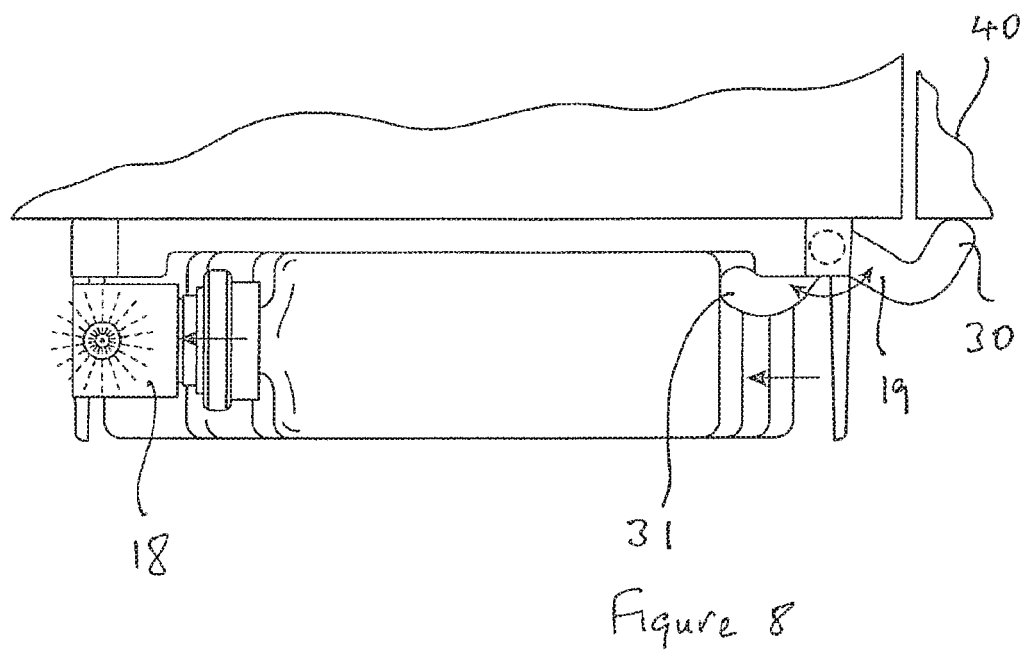
FIG. 8 is an underneath schematic view of the apparatus of FIG. 6 with the door in a closed position.
Figure 9:
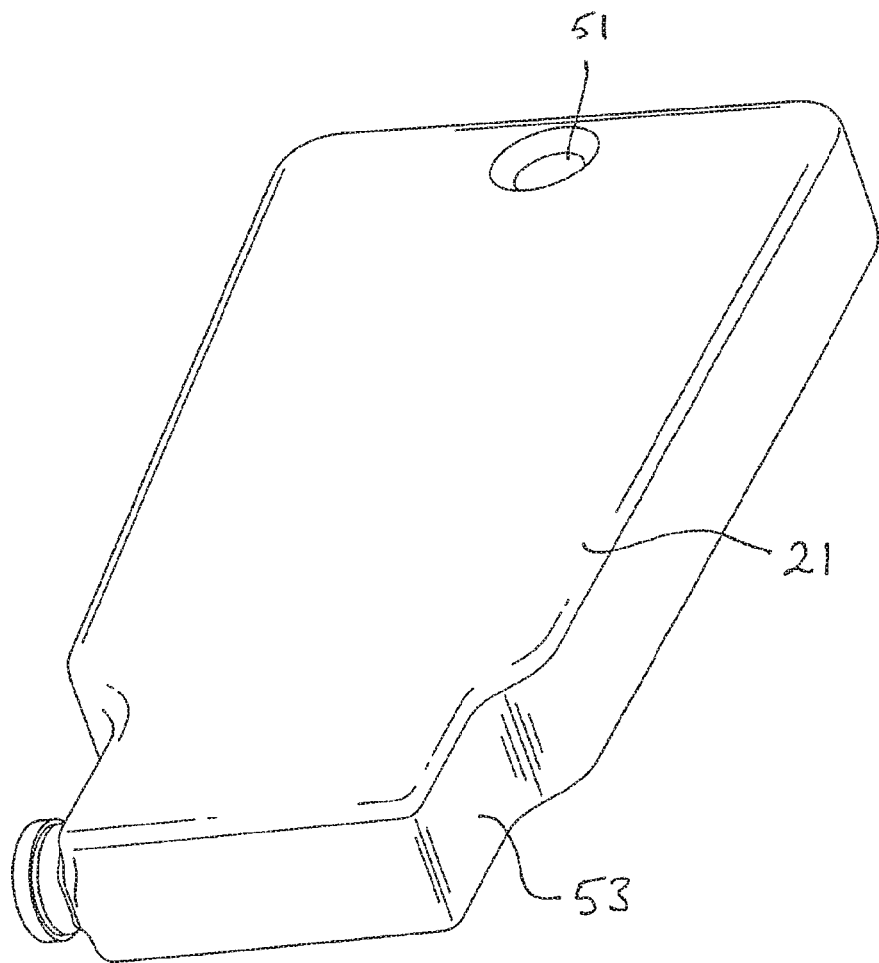
FIG. 9 is a perspective view of the container of FIG. 6.
Figure 10:
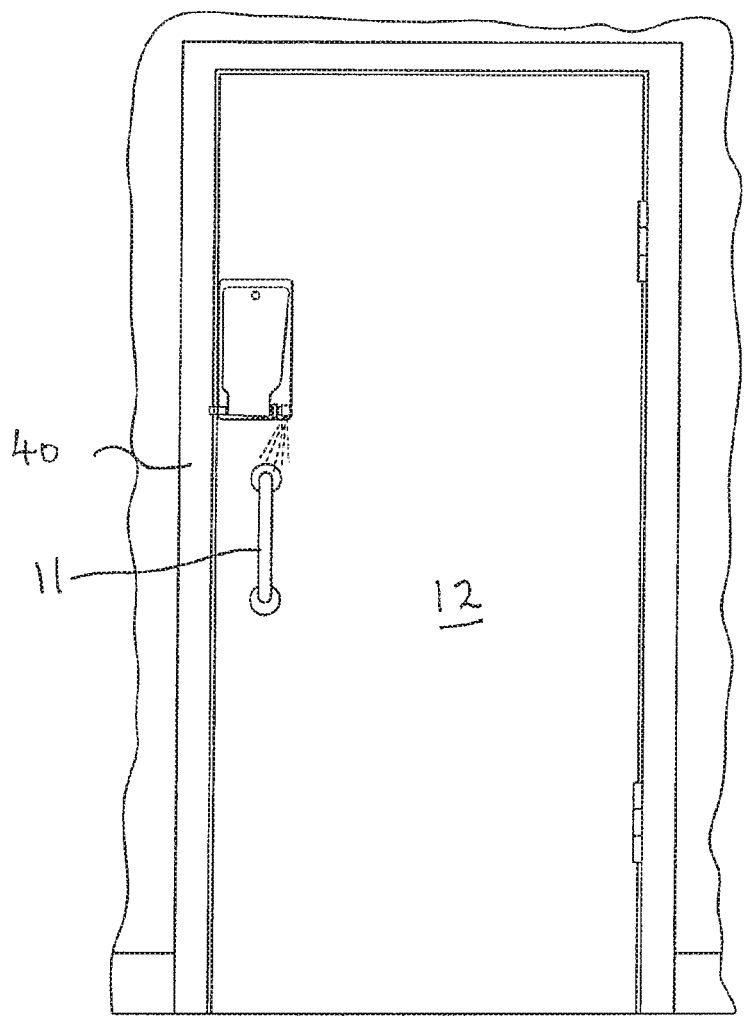
FIG. 10 is a schematic view of a "left hand" version of the apparatus of FIG. 5 mounted on a door.
Figure 12:
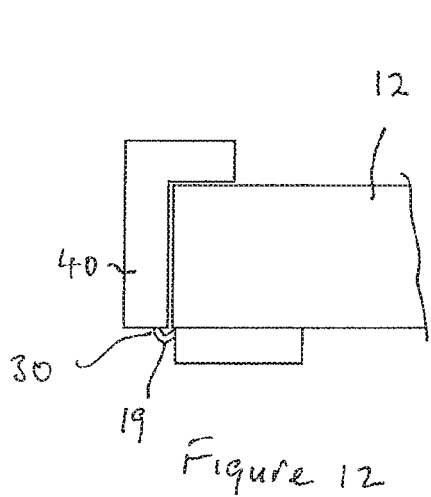
FIG. 12 is a schematic view of the device with the door in a closed position.
Figure 11:
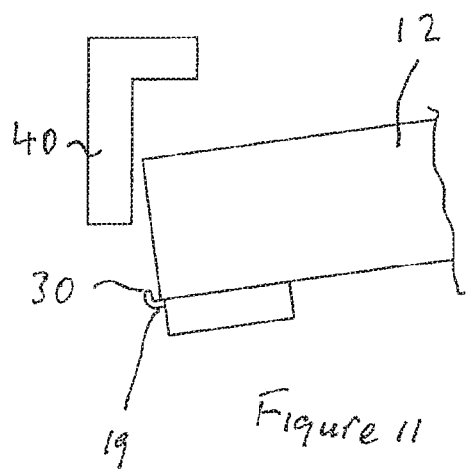
FIG. 11 is a schematic view of the door and device in an open position.

In FIGS. 10, 11 and 12 there is shown the apparatus of FIG. 5 mounted to a door 12. In this embodiment, the apparatus is arranged for mounting to a left hand opening door. In FIGS. 7 and 8, there is shown the door in the open position (FIG. 7) and in the closed position (FIG. 8). When the door is closed, the door frame engaging portion 30 of the actuating arm 19 abuts against the door frame 40 causing the actuating arm 19 to pivot so that the cam portion 31 engages against the side wall 53 of the container 21 causing the container to move within the housing and to operate the spray head 18. When the door is opened, the bias of the spray head 18 acts against the container 21 to move the container to its initial position and to also move the actuating arm 19 to its initial position as shown in FIG. 7. It will be noted in FIG. 7 that the door frame engaging portion 30 of the actuating arm 19 projects forwardly of the plane of the surface of the door on which the apparatus is mounted.

This embodiment of the invention has considerable advantages particularly in that the number of parts is considerably reduced and therefore the cost of production is low and the reliability of the apparatus is extremely good.

The embodiments of the invention have the advantage that they provide a simple inexpensive and reliable apparatus to enable a spray of disinfectant liquid to be applied to a door handle, door push plate or other door surface when a door is opened or closed. In this regard, it will be appreciated that the apparatus could be arranged to apply the spray of disinfectant liquid onto the door handle when the door is being opened rather than when it is being closed.

Figure 13:
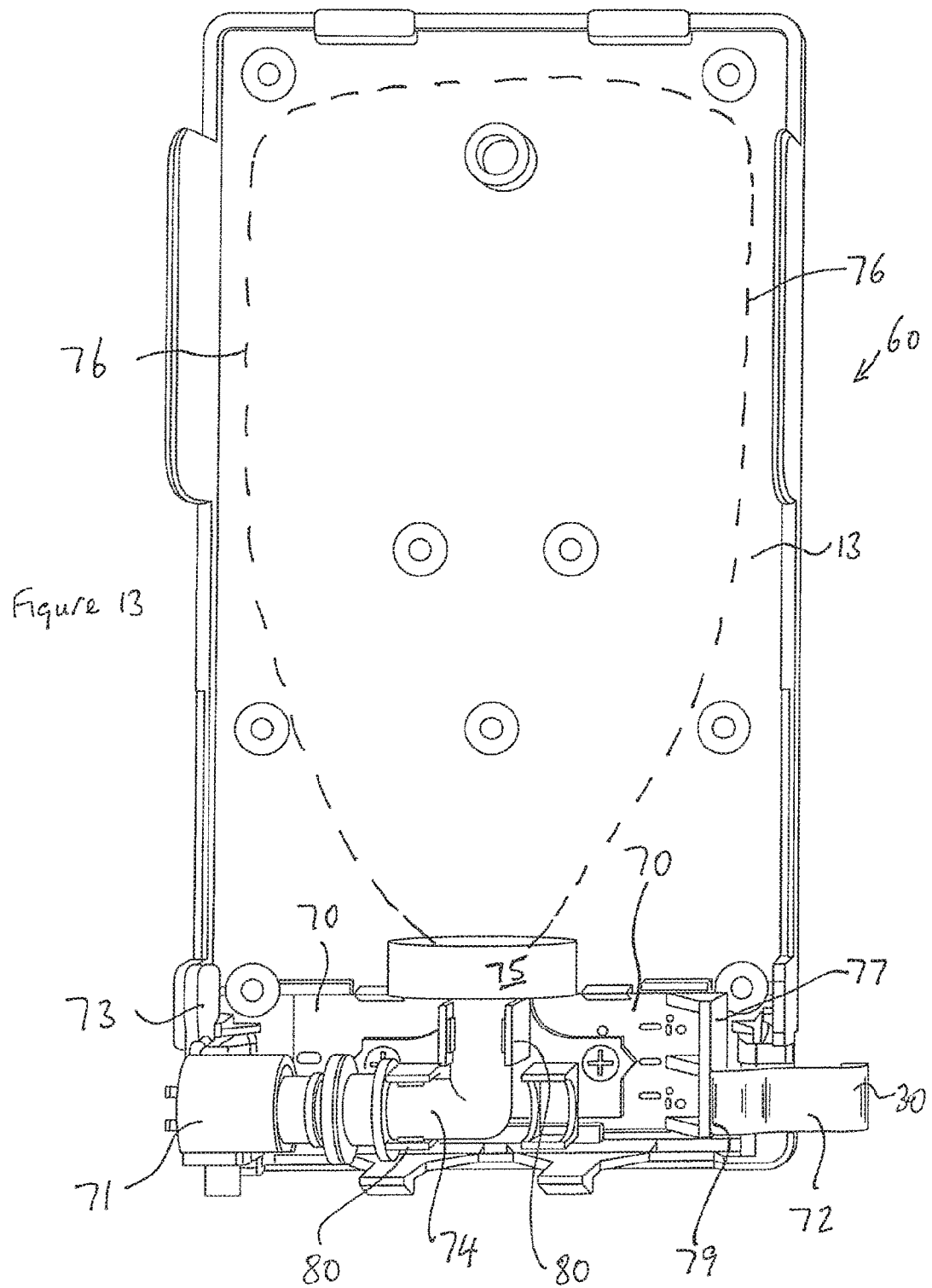
FIG. 13 is a schematic view of another embodiment of a cleaning device according to the invention.
Figure 14:
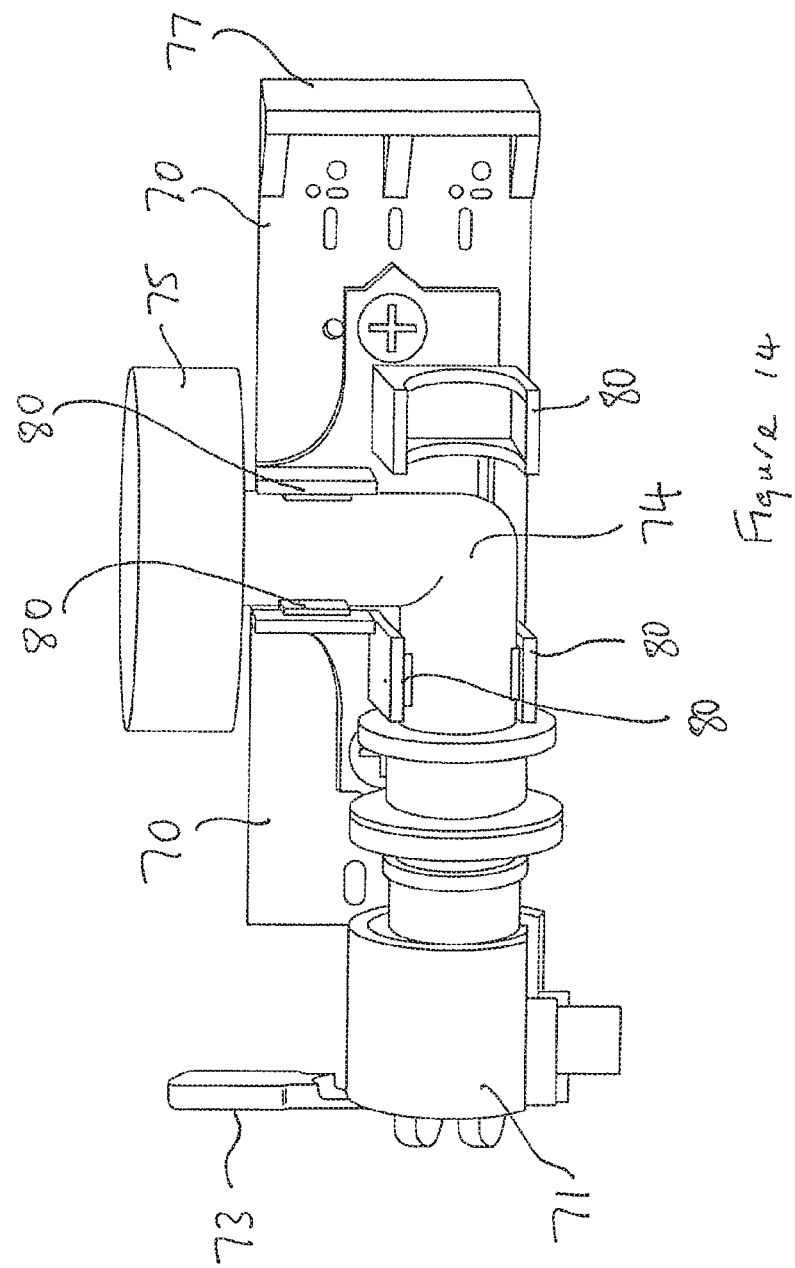
FIG. 14 is a schematic view of the slidable arm (slider) of the apparatus of FIG. 13.

Referring now to FIGS. 13 and 14 there is shown therein another embodiment of a cleaning device generally indicated at 60 according to the invention. This embodiment is useful where is desirable to use a flexible bag or pouch type of liquid container or reservoir. The device 60 has a base 13, the lower portion of which has a moveable slidable arm (slider) 70 mounted thereon. A spray head 71 is disposed at one end of the base and an actuating arm 72 is mounted at the opposite end. A flange 73 on the spray head 71 abuts against a sidewall of the base 13. The spray head 71 is connected by a conduit 74 via a boss 75 to a flexiable bag or pouch type of container shown in dotted outline at 76.

The slider 70 has a cam surface 77. The actuating arm 72 is mounted on the base 13, as described previously in relation to the previous embodiments and also in relation to the following embodiments. A cam portion 79 of the actuating a 72 engages the cam surface 77 of the slider 70 so that movement of the arm 72 and cam portion 79 causes the slider 70 to move against the spray head 71 and cause activation of the spray head, to spray a disinfectant liquid onto a door handle or door push plate.

The conduit 74 may be engaged in spring urged clips 80 mounted on the slider 70. It is envisage that the flexible bag or pouch 76, the boss 75 together with the conduit 74 and the spray head 71 may if desired be supplied as a "refill" so that when a bag 76 is empty it may be removed including the conduit 74 and spray head 71 and replaced with a complete new system.

It will be clear therefore that the invention further provides a refill container of disinfectant fluid having a conduit connected to a spray head, for a cleaning device.

Further the invention provides a refill container of disinfectant fluid having a conduit for connecting to a spray head.

It will be clear that the actuating member 72 is similar to that of the actuating member 19 described in relation to the other embodiments and that the components and parts of the various embodiments are interchangeable.

Figure 15:
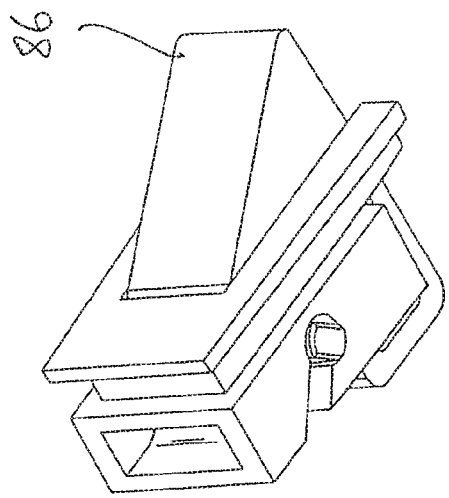
FIG. 15 is a perspective view of another embodiment of an actuating arm for an outwardly opening door according to the invention.
Figure 16:
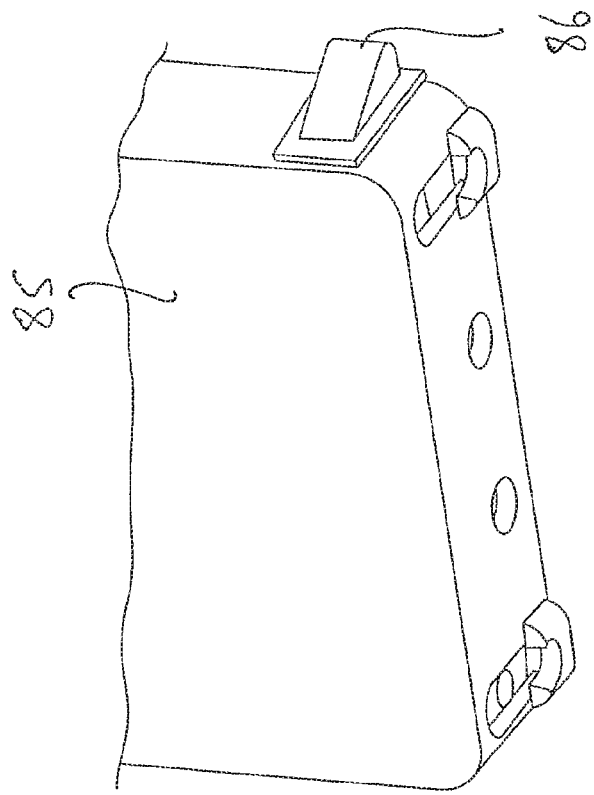
FIG. 16 is a perspective view of a cleaning device according to the invention incorporating the actuating arm of FIG. 15.

Referring now to FIGS. 15 and 16 there is shown another embodiment of a cleaning device 85 according to the invention having an actuating arm for an outwardly opening door according to the invention. In this embodiment the interior of the device 85 may be similar to the other embodiments described herein and in this case the main difference is that the actuating arm 86 is generally wedge shaped. In the closed position of the door, the arm 86 is pivoted inwardly against the bias of the spray head by the door frame so that the spray is activated as the door is closed and when the door is opened the arm is released to ready the apparatus to spray again when the door is next closed.

Referring now to FIGS. 17-20 there is shown another embodiment of cleaning apparatus 90 according to the invention. In this embodiment the actuating arm 85 is separate from the housing. The actuating arm 85 is mounted in the interior of the door structure and comprises a spring urged arm 85 which has an end which engages with the door frame. The actuating arm has an extension part 87 having several holes 88, to receive a trigger pin 89 which projects from the rear of the apparatus 90. The trigger pin 89 is engaged inside the housing 90 with a slidable arm (slider) not shown.

The door 95 has a hole 96 cut in it to enable the trigger pin 89 to engage with one of the holes 88 in the extension part 87 of the actuating arm 85.

Therefore, when the door closes the arm 85 is pushed inwardly into the door 95 and with the pin 89 engaged in a hole 88, in the extension part 87, the pin moves the slider (inside the housing 90) to activate the spray head.

It will be appreciated that suitable means may be provided to enable positional adjustment of the spray head, in all embodiments of the invention, so that the angle of the spray can be adjusted for optimal effect. Such positional adjustment of the spray head can be achieved, for example, by providing suitable pins or holding elements on the base 13 which enable the spray head to be located and held as desired.

The invention has particular applications in many environments including hospitals, restaurants and other areas where members of the public are present. The invention will greatly assist in minimising and eliminating the spread of bacteria and infection from doors, door surfaces and door handles by reducing or eliminating contamination on the surfaces which are regularly touched by many individuals.

The invention also has the advantage that it does not require a cam mounted on the door frame to actuate the spray head since the actuating arm can engage directly with the door frame. In particular, the actuating arm can be made of a plastics material which is suitably contoured and moulded to minimise any impact with the door frame.

The invention is not limited to the embodiment described herein which may be modified or varied without departing from the scope of the invention.

The invention claimed is:

1. A cleaning device for door handles and door push plates comprising: a housing for mounting on a door, the door having a handle or push plate disposed beneath the housing, the door being mounted in a door frame, the housing having a reservoir for disinfectant liquid and a spray head, an actuating arm rotatable in a first plane and having a door frame engaging portion which projects outwardly from the housing and is in use operatively associated with the door frame in which the door is mounted, the actuating arm having an actuating portion, and the reservoir being pivotally mounted within the housing such that it is rotatable in a second plane and by the actuating portion of the actuating arm, wherein when the door frame engaging portion of the actuating arm engages with the door frame the actuating portion of the actuating arm moves rotationally in the first plane and causes the reservoir to rotate in the second plane, the first and second planes not being co-planar, the rotation of the reservoir operates the spray head to discharge a predetermined amount of disinfectant liquid spray downwardly onto the door handle or push plate.

2. A cleaning device as claimed in claim 1 wherein the door frame engaging portion of the actuating arm projects forwardly of a plane of the housing which abuts the door.

3. A cleaning device as claimed in claim 1 wherein the actuating portion is disposed within the housing and arranged to move the reservoir to activate the spray head.

4. A cleaning device as claimed in claim 3 wherein the actuating portion comprises a cam portion.

5. A cleaning device as claimed in claim 3 wherein the actuating arm is pivotally mounted to said housing.

6. A cleaning device as claimed in claim 1 wherein the reservoir for disinfectant liquid is a container of solid wall construction.

7. A cleaning device as claimed in claim 6 wherein the reservoir has the spray head attached thereto.

\* \* \* \* \*